(12) United States Patent
Schall et al.

(10) Patent No.: US 9,168,083 B2
(45) Date of Patent: Oct. 27, 2015

(54) HR SURGICAL GENERATOR

(75) Inventors: Heiko Schall, Nuertingen (DE); Florian Eisele, Freiburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 997 days.

(21) Appl. No.: 13/062,681

(22) PCT Filed: Aug. 10, 2009

(86) PCT No.: PCT/EP2009/005797
§ 371 (c)(1),
(2), (4) Date: Mar. 7, 2011

(87) PCT Pub. No.: WO2010/025807
PCT Pub. Date: Mar. 11, 2010

(65) Prior Publication Data
US 2011/0170321 A1      Jul. 14, 2011

(30) Foreign Application Priority Data

Sep. 8, 2008  (DE) .......................... 10 2008 046 247
Nov. 24, 2008  (DE) .......................... 10 2008 058 737

(51) Int. Cl.
*A61B 18/12*  (2006.01)
*H03L 5/00*  (2006.01)
*A61B 18/00*  (2006.01)

(52) U.S. Cl.
CPC .............. *A61B 18/1206* (2013.01); *H03L 5/00* (2013.01); *A61B 2018/00577* (2013.01);
(Continued)

(58) Field of Classification Search
CPC ................. A61B 18/1206; A61B 2018/00875; A61B 2018/00702; A61B 2018/00827; A61B 2018/00678; A61B 2018/00642; A61B 2018/00648; A61B 2018/00779; A61B 17/32; A61B 18/04
USPC ........... 606/32, 33, 34, 40, 41; 363/21.14, 89, 363/40, 65, 132, 16; 323/234, 84, 283, 275, 323/267
See application file for complete search history.

(56) References Cited

U.S. PATENT DOCUMENTS 4,727,874 A * 3/1988 Bowers et al. .................. 606/38
4,823,251 A * 4/1989 Kawabata et al. ............. 363/95
(Continued)

FOREIGN PATENT DOCUMENTS

CN      1983785 A      6/2007
DE   102 18 895 B4   12/2006
(Continued)

OTHER PUBLICATIONS

Database WPI Week 200781, Thompson Scientific, London, GB; AN 2007-875007, XP-002551484 (1 page).

*Primary Examiner* — Ronald Hupczey, Jr.
(74) *Attorney, Agent, or Firm* — Dickstein Shapiro LLP

(57) ABSTRACT

A high-frequency surgical generator including a power supply for supplying rectified electrical energy, a power oscillator for supplying a potential-free, DC current-free and DC voltage-free high frequency voltage and a control device for controlling the high frequency voltage wherein the power supply is configured as a current source for supplying a load-independent output current, such that the load-independent output current of the power supply serves as the control variable for controlling the high-frequency voltage. The target value of the load-independent output current is pre-determined by the control device. The high-frequency surgical generators configured as such achieve improved modulation capability.

16 Claims, 4 Drawing Sheets

(52) U.S. Cl.
CPC ............... *A61B 2018/00601* (2013.01); *A61B 2018/00642* (2013.01); *A61B 2018/00767* (2013.01); *A61B 2018/00892* (2013.01)

(56) References Cited

U.S. PATENT DOCUMENTS

| | | | |
|---|---|---|---|
| 5,088,016 A * | 2/1992 | Vinciarelli et al. | 363/15 |
| 5,167,658 A * | 12/1992 | Ensslin | 606/34 |
| 5,304,214 A | 4/1994 | DeFord et al. | |
| 5,836,943 A | 11/1998 | Miller, III | |
| 6,195,275 B1 * | 2/2001 | Lu | 363/65 |
| 6,288,589 B1 * | 9/2001 | Potter et al. | 327/295 |
| 6,293,941 B1 * | 9/2001 | Strul et al. | 606/34 |
| 6,310,785 B1 * | 10/2001 | Ayyanar et al. | 363/17 |
| 6,812,842 B2 | 11/2004 | Dimmer | |
| 6,939,347 B2 * | 9/2005 | Thompson | 606/34 |
| 2002/0165530 A1 * | 11/2002 | Harano et al. | 606/32 |
| 2002/0165539 A1 | 11/2002 | Durgin et al. | |
| 2003/0058659 A1 * | 3/2003 | Klinkowstein | 363/17 |
| 2004/0097915 A1 * | 5/2004 | Refior et al. | 606/34 |
| 2005/0143725 A1 | 6/2005 | Daners et al. | |
| 2005/0149012 A1 * | 7/2005 | Penny et al. | 606/41 |
| 2007/0093801 A1 * | 4/2007 | Behnke | 606/34 |
| 2008/0009850 A1 * | 1/2008 | Goble et al. | 606/37 |
| 2008/0055942 A1 * | 3/2008 | Tao et al. | 363/21.03 |
| 2008/0082096 A1 * | 4/2008 | Shores et al. | 606/34 |
| 2008/0239770 A1 * | 10/2008 | Punzet et al. | 363/40 |

FOREIGN PATENT DOCUMENTS

| | | |
|---|---|---|
| EP | 1 543 788 A2 | 6/2005 |
| JP | 2000-254142 A | 9/2000 |
| JP | 2002-360712 A | 12/2002 |
| JP | 2005-513450 A | 5/2005 |
| JP | 2007-111529 A | 5/2007 |
| WO | WO 2007/002262 A2 | 1/2007 |
| WO | WO 2008/053532 | 5/2008 |

* cited by examiner

PRIOR ART

HR SURGICAL GENERATOR

CROSS-REFERENCE TO RELATED APPLICATIONS

This application is a National Stage Entry of International Application No. PCT/EP2009/005797, filed Aug. 10, 2009, which claims priority to DE 10 2008 046 247.0 filed Sep. 8, 2008 and to DE 10 2008 058 737.0 filed Nov. 24, 2008.

FIELD OF THE INVENTION

The disclosed embodiments relate to a high-frequency surgical generator and to a method for generating a high-frequency voltage in a high-frequency surgical generator.

BACKGROUND

High-frequency surgical devices are increasingly being used in surgery. The generators employed for this purpose supply a fundamental frequency, which typically lies in the range of 300 kHz to 4 MHz. In the generators, power oscillators are provided which rectify and convert electrical energy provided from the main supply network into a potential-free, DC voltage-free output voltage having the aforementioned fundamental frequency. In very many applications, such as high voltage coagulation or coagulating cutting, this fundamental frequency is overlaid with a 'modulation frequency', which is typically in the order of 50 kHz. A limited number of sinusoidal oscillations (in an extreme case, a single sinusoidal oscillation) is to be generated, followed by a pulse pause without any energy transfer. Following expiration of a modulation period, the provision of a pulse packet begins again.

It is evident from this that spontaneous starting of the output voltage is required. This means that after 1 or, at most 2, half-periods, the output voltage must have reached its end value, since this influences the effect being striven for on the tissue being treated.

Usually, the energy conversion described is brought about in two successive steps, as illustrated by FIG. 7. First, the electrical energy supplied from the main 1 is rectified by a rectifier 2, so that a constant DC voltage is made available. This constant DC voltage is converted by a power supply 3 (a DC/DC converter) into an intermediate circuit voltage $U_Z$. This intermediate circuit voltage $U_Z$ is adjustable. This first energy conversion unit will be referred to in the following as the power supply.

Connected thereto is a second energy conversion unit, which will be referred to in the following as the power oscillator 10. The power oscillator 10 is an inverter, which also includes a potential separation from the patient circuit. The output terminals of the power oscillator 10 are connected, on one side, to an electrosurgical instrument 4 and, on the other side, to a neutral electrode 5. Also connected to the output terminals of the power oscillator 10 is an actual-value sensor 22, which detects the voltage at the output of the power oscillator 10 and compares said voltage with a target voltage from a setpoint generator 21, whereupon the system deviation is fed back to the power supply 3 via a controller 20, so that the intermediate circuit voltage $U_Z$ is adjusted such that the output voltage amplitude of the power oscillator 10 is controlled according to the setting of the setpoint generator 21.

As shown in FIGS. 8 and 9, the power oscillator 10 usually includes a driving circuit 11 with power semiconductor devices, a transformer 12, which is enhanced with a parallel connected capacitance $C_P$ into a parallel resonant circuit and, at the output of the transformer 12, a series circuit including an inductance $L_{SA}$ and a capacitance $C_{SA}$, that is, a series resonant circuit toward the patient circuit. In the conventional embodiment shown in FIG. 9, a further series resonant circuit including an inductor $L_{SE}$ and a capacitor $C_{SE}$ is also provided between the output terminals of the driving circuit 11 and the parallel resonant circuit comprising the transformer 12 and the parallel capacitance $C_P$.

In order to ensure the best possible modulation capability and therefore the spontaneous starting of the oscillation of the output voltage, the input series resonant circuit (as per FIG. 9) is often dispensed with (as shown in FIG. 8). The input of the overall resonant circuit is therefore a parallel resonant circuit. Since the driving circuit is also fed from a voltage source, specifically an output capacitance $C_A$ of the power supply 3, the driving power semiconductor device 11 represents a short-circuit between a charged capacitor ($C_A$) and an uncharged capacitor ($C_P$). The consequence thereof is that the size of the current flowing is determined only by parasitic manifestations such as lead inductances and path resistances of the semiconductor devices. Since these parasitic values are usually small compared with the actual component values, very high undefined electrical current values arise. These, often very high, pulsed currents can emit undesirable electromagnetic interference (which is not permissible in clinical environments). In addition, the dimensioning of the power semiconductor devices of the driving circuit 11 is often uneconomic.

In order to solve this problem, the circuit shown in FIG. 9 is used, wherein the driving currents are determined by an input inductance $L_{SE}$. However, this brings with it the disadvantage that the filter does not start to oscillate spontaneously and is therefore not suitable for the aforementioned modulation.

SUMMARY

It is an object of the disclosed embodiments to provide a high-frequency surgical generator and a method for generating a high-frequency voltage in a high-frequency surgical generator such that a good modulation capability is achieved and the aforementioned disadvantages, particularly excessive currents, are prevented.

Disclosed embodiments include a high-frequency surgical generator including a power supply for supplying rectified electrical energy, a power oscillator for supplying a potential-free, DC current-free and DC voltage-free high frequency voltage, and a control device for controlling the high frequency voltage, wherein the power supply is configured as a current source for supplying a load-independent output current, the target value of which is pre-determined by the control device, such that the load-independent output current of the power supply serves as the control variable for controlling the high-frequency voltage. As opposed to the previously known solutions, the power supply of the disclosed embodiments does not have a load-independent output voltage, but rather outputs a load-independent, controlled output current. The target value of this output current is pre-determined by the (per se known) control system of the high-frequency surgical device. The load-independent current therefore serves as a control variable for the control of the high-frequency output voltage and of the high-frequency effect on the tissue.

The power supply preferably includes a main rectifier device for converting a main alternating voltage into a substantially constant DC voltage, and an intermediate circuit connected on the output side for supplying adjustable, rectified energy. The power supply preferably includes either a step-down converter or a potential-separating forward converter. No output capacitor is provided in this case. The output of the power supply is therefore an inductance and the control system of the power supply controls the output current, wherein the output voltage is freely adjustable according to the load conditions.

Since the controlled system of the current control system required here—at least after suitable selection of the output inductance, which represents a compromise between structural volume/costs and current ripple—has a very fast time constant, the current controller is suitably realized as a "control system with a finite adjustment time", preferably even as a "dead beat control", particularly in a digital signal processor or another integrated circuit.

In this context, it should be noted that the condition of the power supply in which no electrical power is delivered is a short-circuit at the output. The device is therefore short-circuit-proof. During load-free running, the voltage would be able to be increased by inductive overvoltage until destruction of a component. It must therefore be ensured by operation of the downstream circuit components (of the power oscillator) that the inductive output of the power supply is never operated load-free.

The power oscillator preferably includes a power electronics driving circuit configured as an H-bridge of semiconductor circuit elements. In order to avoid unwanted power short-circuits during load-free running phases, diodes are preferably provided in series with the semiconductor circuit elements.

The driving circuit is preferably configured such that in an energy-recovery operation, energy stored in reactive components is fed back to the power supply, such that the efficiency of the arrangement is increased. Furthermore, by means of the energy-recovery, postoscillation of the output voltage is prevented, so that the curve shape of the output voltage is reduced to zero as rapidly as possible.

The driving circuit is also preferably configured such that the semiconductor circuit elements are controlled in pairs, in phase-synchronized resonance. Due to the relatively high switching time of 2*50%, moderate current strengths are therefore produced in the power semiconductor components, which are therefore very favorably utilized.

If the energy-recovery capability is dispensed with, two power semiconductor devices (as compared with four) can be spared. For the supply, either two current sources (power supplies), which are controlled independently of one another, are constructed, or the circuit is fed from one current-regulated power supply and the two branches are divided via inductive current dividers.

The method according to the disclosed embodiments for generating a high-frequency voltage in a high-frequency surgical generator includes the generating of rectified electrical energy in a power supply, generating a potential-free, DC current-free or DC voltage-free regulated high frequency voltage, wherein the power supply supplies a load-independent output current with a pre-determined target value, so that the load-independent output current of the power supply regulates the high-frequency voltage as the control variable.

BRIEF DESCRIPTION OF THE DRAWINGS

Preferred example embodiments of the invention are described in detail below, making reference to the drawings.

DETAILED DESCRIPTION

In the following description, the same reference signs and designations are used for the same and similarly acting parts.

Figure 1:
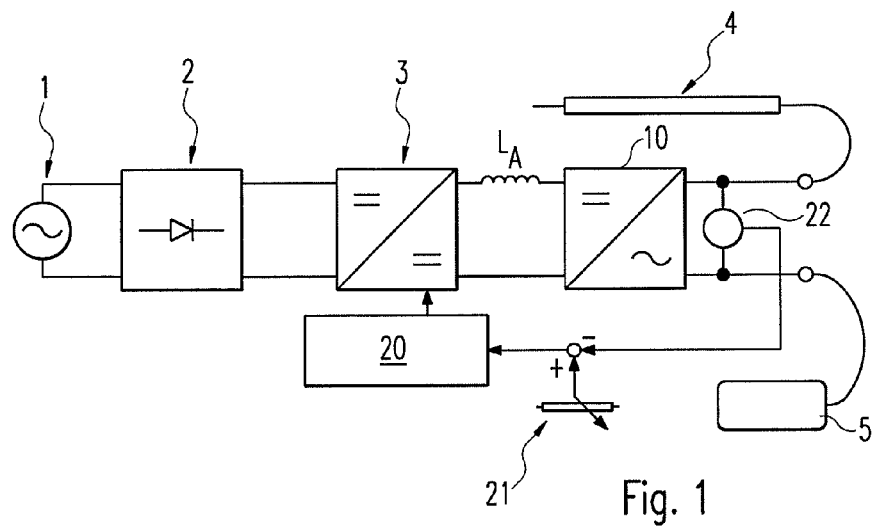
FIG. 1 is a schematic representation of a high-frequency surgical generator.
Figure 7:
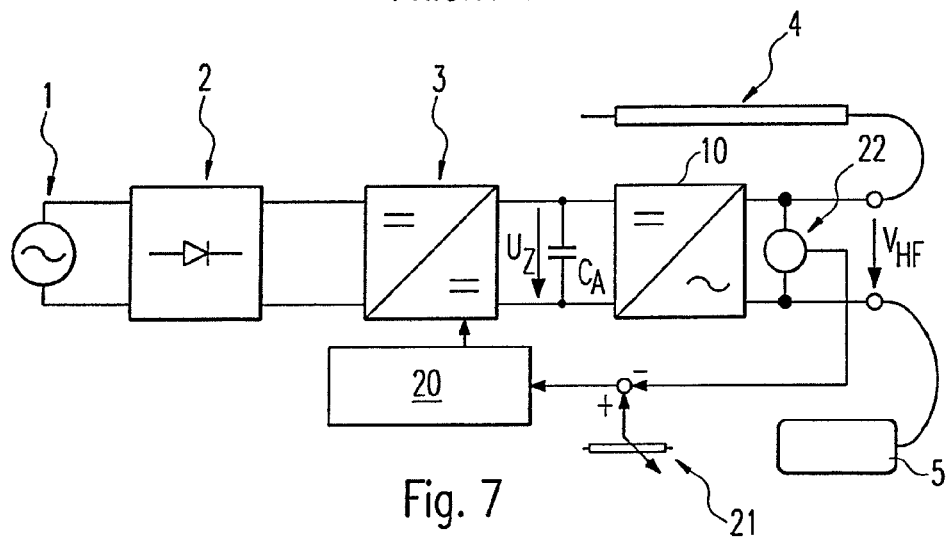
FIG. 7 is a representation of a known high-frequency surgical generator.
Figure 8:
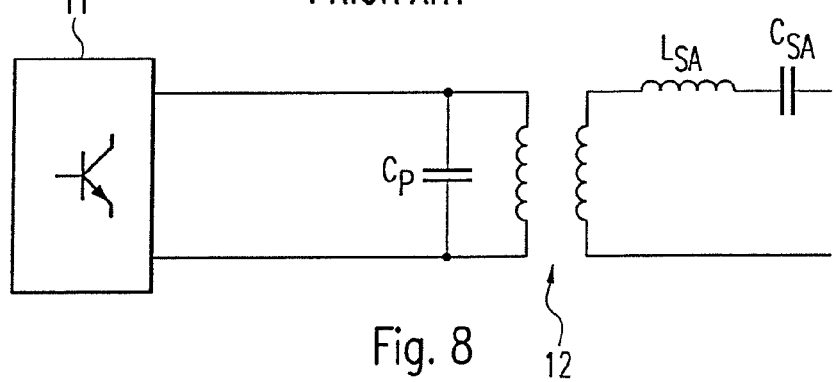
FIG. 8 illustrates a first type of known power oscillator.
Figure 9:
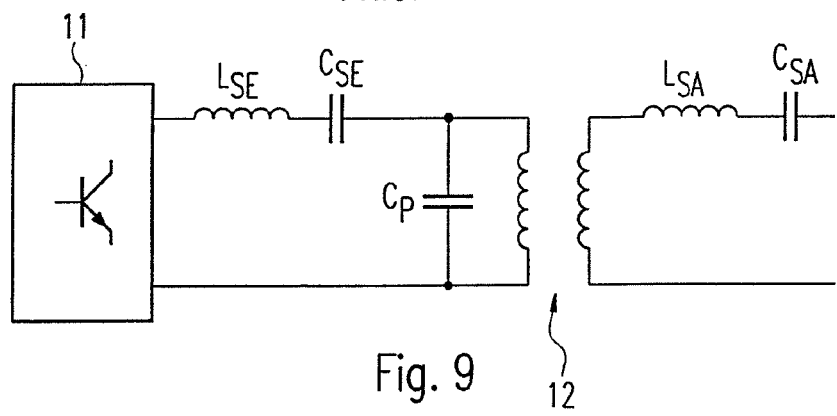
FIG. 9 illustrates a second type of known power oscillator.

The fundamental structure of the example embodiment of the high-frequency surgical generator described here and illustrated in FIG. 1 generally corresponds to the prior art, as described above with reference to FIGS. 7-9. However, an essential difference lies in the power supply 3, which, in the prior art, provides a constant voltage $U_Z$ at a capacitor $C_A$ connected in parallel to the output thereof, whereas the power supply 3 according to the disclosed embodiments supplies a load-independent output current via an output inductance $L_A$ to the power oscillator 10.

Figure 2A:
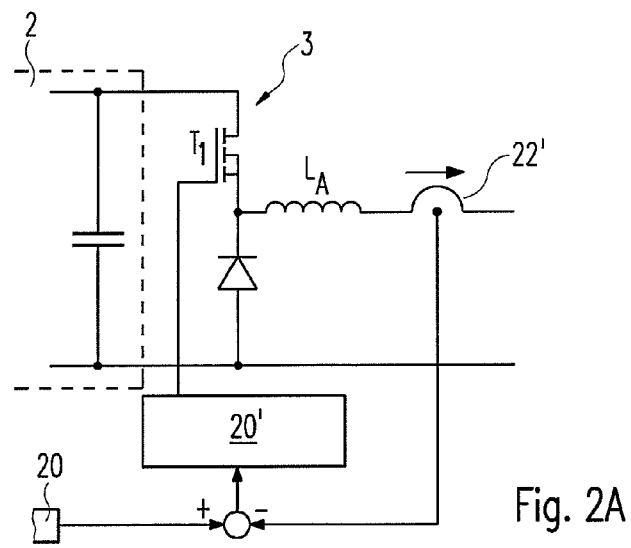
FIG. 2A illustrates a first embodiment of a power supply for the high-frequency surgical generator according to FIG. 1.

FIG. 2A shows a first embodiment of a power supply 3 which obtains the constant input DC voltage from a rectifier 2 with a filter capacitor connected to the output thereof. This power supply 3 is designed as a step-down converter (although without a capacitor at the output) and includes a series connection of a switching transistor $T_1$ and a diode, to the coupling point of which the power oscillator 10 is coupled via the output inductance $L_A$. The current flowing is passed by an actual-value sensor 22' to a subtraction circuit, which compares the current actual value with the current target value, which comes from the known aforementioned controller 20. The comparison value represents a system deviation that is notified to a controller 20'. Said controller 20' controls the transistor $T_1$ such that the desired output current is set.

Figure 2B:
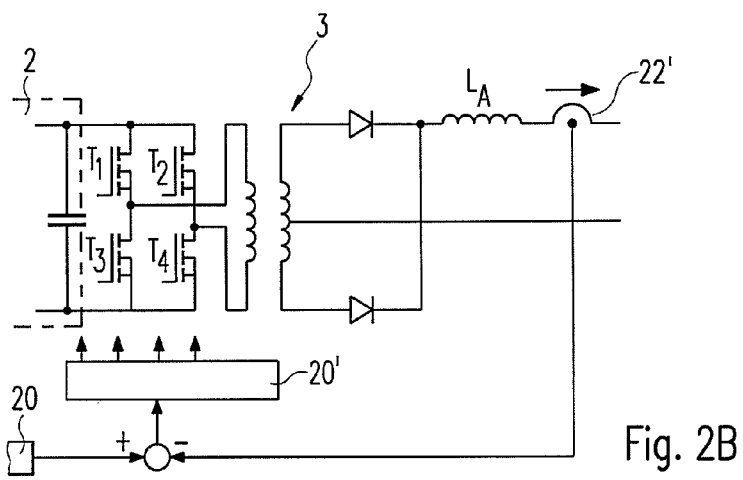
FIG. 2B illustrates a second embodiment of a power supply for a high-frequency surgical generator according to FIG. 1.

The variant of the power supply 3 shown in FIG. 2B shows a potential-separating flow converter, as is per se known. In this case, four switching transistors $T_1$, $T_2$, $T_3$ and $T_4$ are provided, which are arranged in an H-circuit. A primary winding of a respective transformer is connected to each of the coupling points of the transistors $T_1$ and $T_3$, and $T_2$ and $T_4$, the secondary windings thereof which are coupled to one another are connected via diodes to the output inductance $L_A$. The coupling point of the secondary windings forms the second output terminal of the power supply 3. Control is performed similarly to that according to FIG. 2A.

Figure 3:
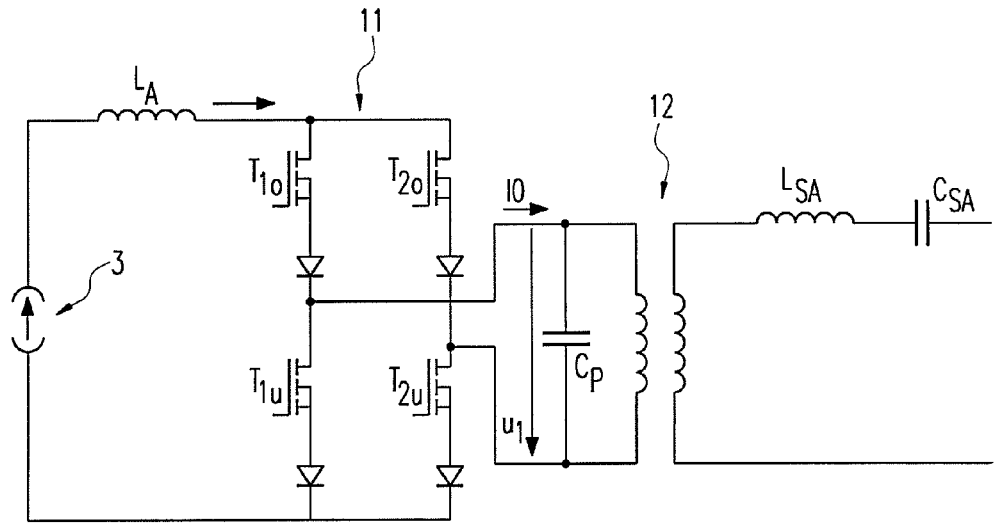
FIG. 3 illustrates a first embodiment of a power oscillator for a high-frequency surgical generator according to FIG. 1.

The power electronics of the driving circuit for the power oscillator will now be described making reference to FIGS. 3 and 4.

The power oscillator 11 is configured as a X-filter. The power electronics of the driving circuit are configured, as per FIG. 3, as an H-bridge with two pairs of transistors $T_{1o}$ and $T_{1u}$, and $T_{2o}$ and $T_{2u}$. Additionally, to prevent unwanted load short-circuits during load-free running phases, diodes are provided in series with the power transistors. Connected to the coupling points of the transistor pairs ($T_{1o}$ and $T_{1u}$, and $T_{2o}$ and $T_{2u}$) is the primary winding of the transformer 12 with the capacitor $C_P$ in parallel therewith. Connected to the output or to the secondary winding of the transformer 12 is the output series resonant circuit $L_{SA}$ and $C_{SA}$. Together with the secondary winding of the transformer 12, the series resonant circuit constitutes part of the patient current circuit.

Figure 4:
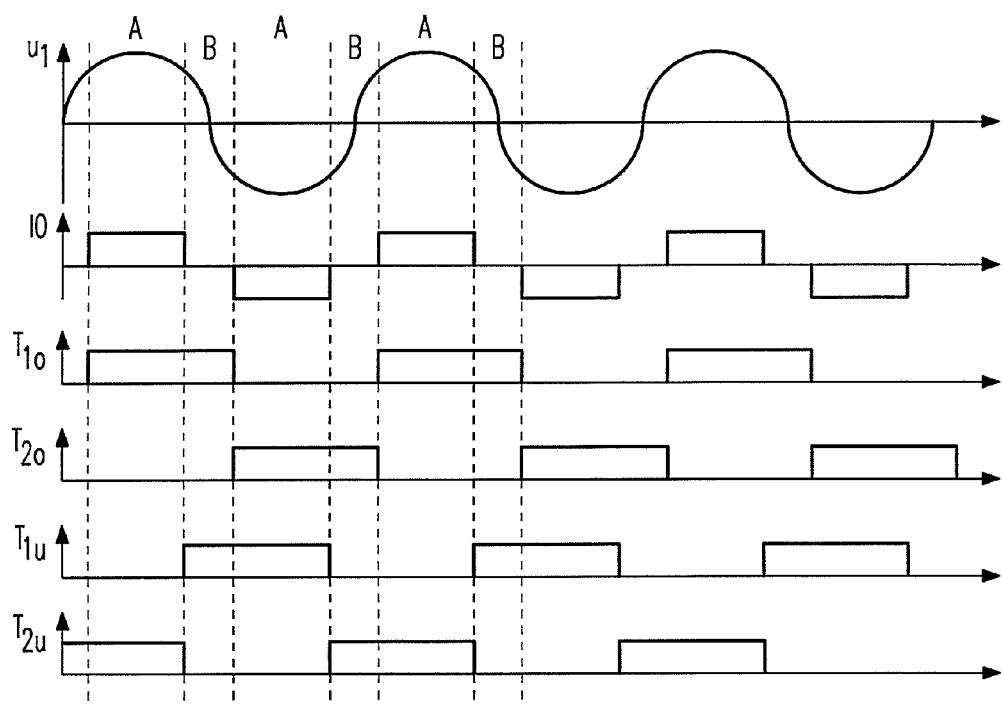
FIG. 4 is a representation of switching functions of power semiconductor devices of the power oscillator according to FIG. 3 together with the voltage/current generated therewith.

Operation of this circuit is designed such that—as shown in FIG. 4—two diagonally opposed power semiconductor devices always conduct simultaneously. To feed the parallel resonant circuit at the output of the H-circuit, therefore, the transistors $T_{1o}$ and $T_{2u}$ or $T_{2o}$ and $T_{1u}$, conduct simultaneously. In the load-free state, when no energy is output by the power supply to the power oscillator, the simultaneous switching on of either $T_{1o}$ and $T_{1u}$, or $T_{2o}$ and $T_{2u}$, that is a half-bridge in each case, is necessary.

A third permitted operating mode is the simultaneous switching on of all four transistors, to bring about energy-recovery operation for the energy found in the reactive components of the power oscillator 11 to the output inductance $L_A$ of the power supply 3. With this type of energy-recovery, the post-pulse oscillation of the output voltage can be prevented and the shape of the output voltage curve is reduced to zero as quickly as possible.

The circuit has further interesting properties for the dimensioning thereof. Specifically, it is possible to drive the circuit in a relative switching time (duty cycle) of almost 100%. For this purpose, the switches $T_{1o}$ and $T_{2o}$ are closed for as long as the voltage across the parallel resonant circuit ($12/C_P$) is positive. This ensures phase-synchronous switching, which operates the circuit in resonance, as shown in FIG. 4. This relatively large switching time of 2*50% results in moderate current strengths in the power semiconductor components, which are therefore very economically utilized.

Figure 5:
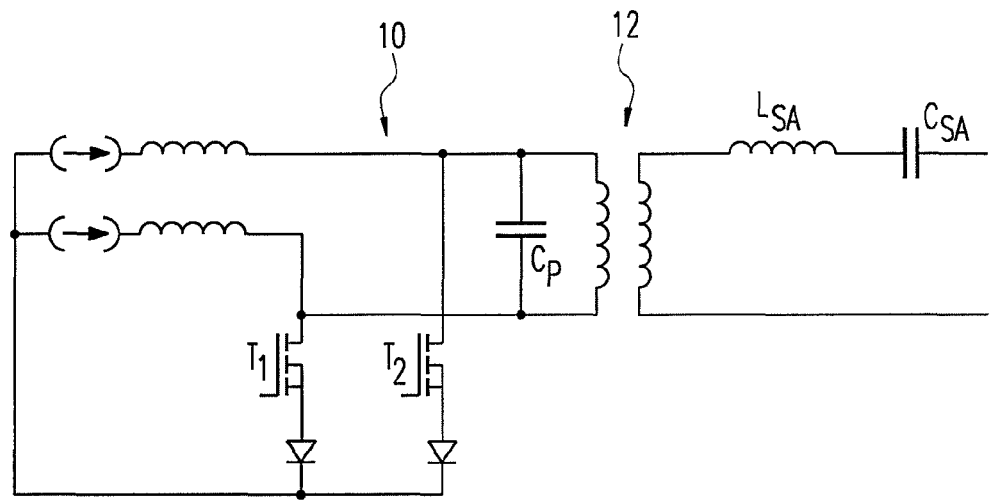
FIG. 5 illustrates a second embodiment of a power oscillator for a high-frequency surgical generator according to FIG. 1.
Figure 6:
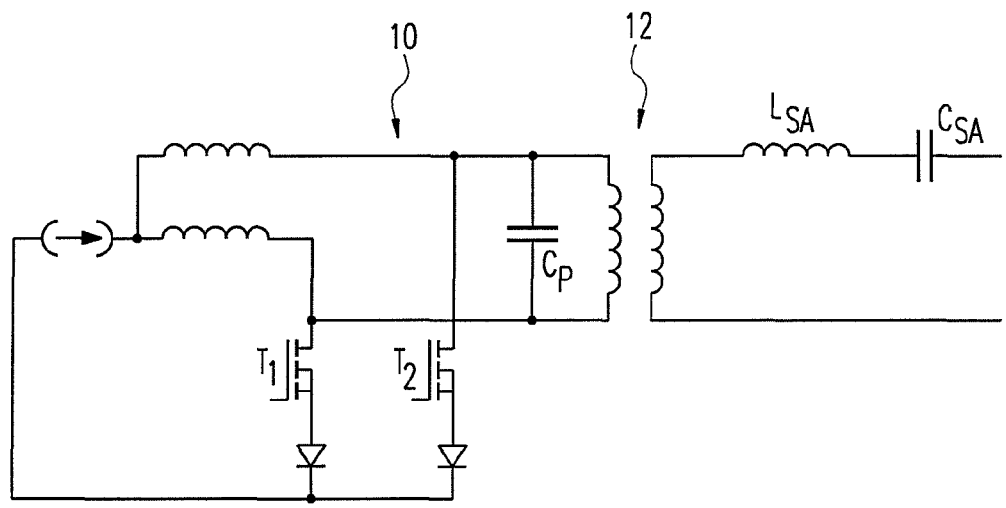
FIG. 6 illustrates a third embodiment of a power oscillator for a high-frequency surgical generator according to FIG. 1.

In the embodiment of the power oscillator 10 shown in FIG. 5, only two power semiconductor components $T_1$ and $T_2$ (with load-free running diodes) are provided, said components having two current sources which are regulated independently from one another. In the variant shown in FIG. 6, only a single current-regulated power supply is provided, whereas the two branches with the power semiconductor components $T_1$ and $T_2$ therein are fed via an inductive current divider.

It is clear from the above that the invention can be realized in many different circuit configurations.

The invention claimed is:

1. A high-frequency surgical generator, comprising:
   a power supply for supplying rectified electrical energy;
   a power oscillator for supplying a high-frequency voltage, the high-frequency voltage being potential-free, DC current-free and DC voltage-free; and
   a control device for controlling the high-frequency voltage by controlling the power supply,
   wherein the power supply is configured as a current source for supplying a load-independent output current, a target value of which is pre-determined by the control device such that the load-independent output current of the power supply serves as the control variable for controlling the high-frequency voltage.

2. The high-frequency surgical generator according to claim 1, wherein the power supply comprises a main rectifier device for converting a main alternating voltage into a substantially constant DC voltage, and an intermediate circuit for supplying adjustable, rectified energy.

3. The high-frequency surgical generator according to claim 1, wherein the power supply comprises a step-down converter.

4. The high-frequency surgical generator according to claim 3, wherein the power supply does not comprise an output capacitor.

5. The high-frequency surgical generator according to claim 1, wherein the power supply comprises a potential-separating forward converter.

6. The high-frequency surgical generator according to claim 5, wherein the power supply does not comprise an output capacitor.

7. The high-frequency surgical generator according to claim 1, wherein the control device comprises a control system with a finite adjustment time.

8. The high-frequency surgical generator according to claim 7, wherein the control system is a dead beat controller.

9. The high-frequency surgical generator according to claim 1, wherein the power oscillator comprises a power electronics driving circuit configured as an H-bridge of semiconductor circuit elements.

10. The high-frequency surgical generator according to claim 9, further comprising diodes provided in series with the semiconductor circuit elements.

11. The high-frequency surgical generator according to claim 9, wherein the driving circuit is configured such that in an energy-recovery operation, energy stored in reactive components is fed back to the power supply.

12. The high-frequency surgical generator according to claim 9, wherein the driving circuit is configured such that the semiconductor circuit elements are controlled in pairs, in phase-synchronized resonance.

13. A method for generating a high-frequency voltage in a high-frequency surgical generator, comprising:
   generating a rectified electrical energy in a power supply; and
   generating a potential-free, DC current-free and DC voltage-free regulated high-frequency voltage,
   wherein the power supply is controlled by a control device to supply a load-independent output current with a pre-determined target value, such that the load-independent output current of the power supply regulates the high-frequency voltage as the control variable.

14. The method according to claim 13, wherein the power supply is regulated by means of a control system having a finite adjustment time.

15. The method according the claim 14, wherein the control system is a dead beat controller.

16. The method according to claim 13, wherein, in an energy-recovery operation, energy stored in reactive components is fed back to the power supply.

* * * * *